CHRYSANTHEMUM PLANT
Filed May 15 1972 2 Sheets-Sheet 1
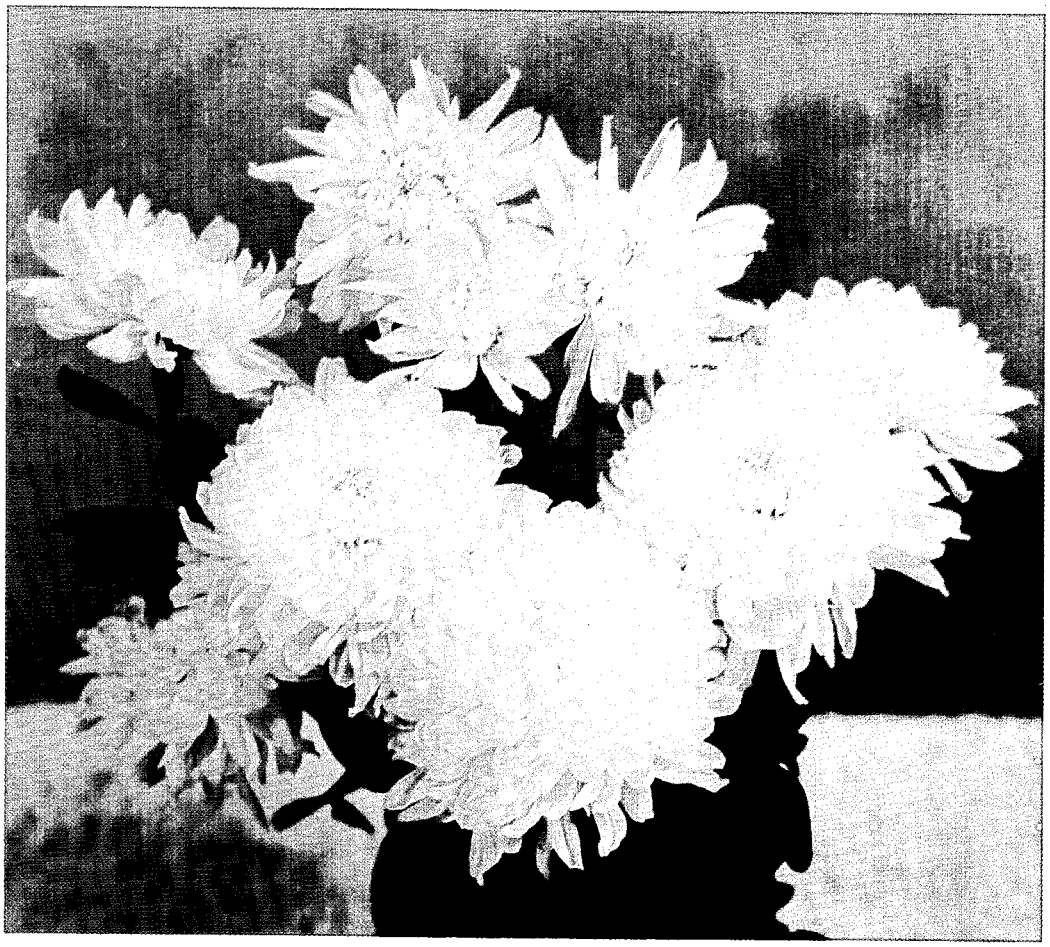

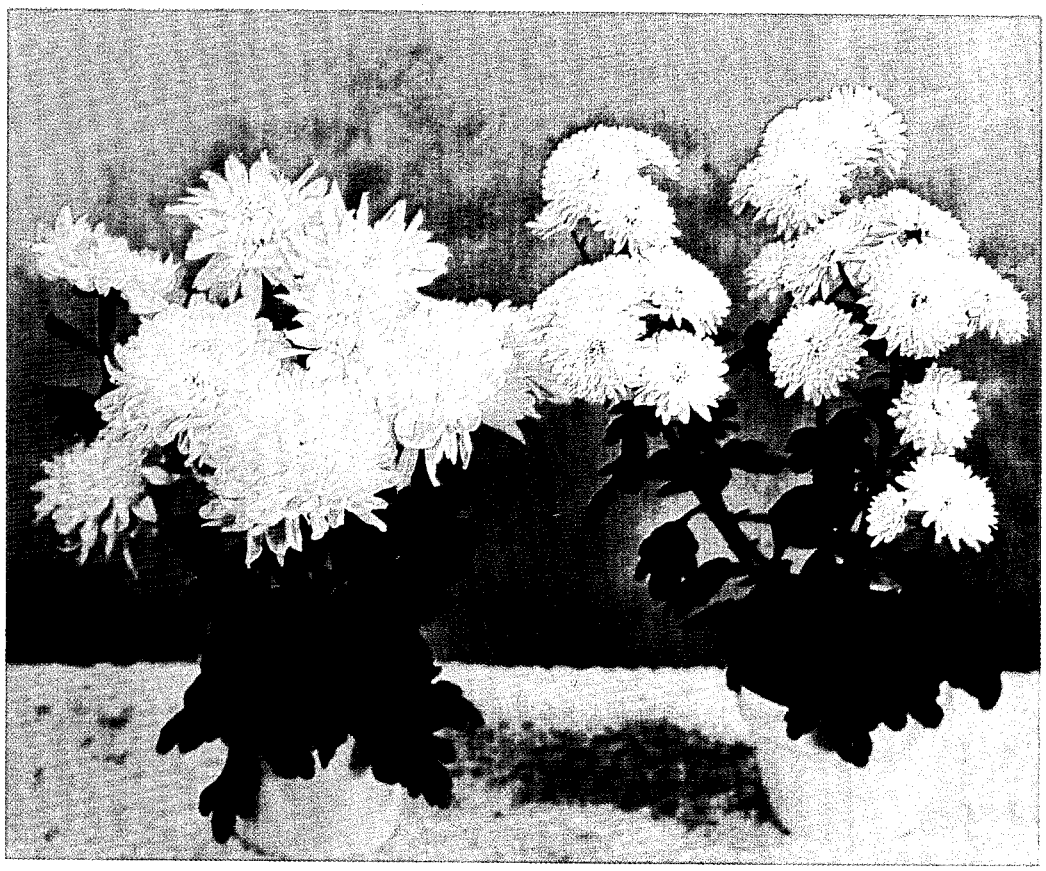

United States Patent Office

Plant Pat. 3,500

Patented Feb. 26, 1974

3,500
CHRYSANTHEMUM PLANT

Grace H. Mack, New Canaan, Conn., and Walter H. Jessel, Jr., Doylestown, and William E. Duffett, Akron, Ohio, assignors to Grace H. Mack, New Canaan, Conn.

Filed May 15, 1972, Ser. No. 253,640
Int. Cl. A01h *5/00*
U.S. Cl. Plt.—75 1 Claim

The present invention comprises a new and distinct cultivar of chrysanthemum plant of the garden variety type which is a seedling of #307–63 x #339–63. Both parents are unpatented and identified for breeding purposes by the above breeding numbers.

The new cultivar is similar in certain respects to the unpatented but commercially well-known garden chrysanthemum variety White Grandchild, having the same characteristics of:

(1) Keeping quality.
(2) Approximate spread of plant.

The new cultivar is distinguished from White Grandchild by the following characteristics, when grown under comparable conditions:

(1) Flowers approximately 2½ inches to 3 inches larger in diameter.
(2) Flowers are more ivory white in color.
(3) Flowers do not pink with age.
(4)) Flowering plants are approximately three inches shorter in height when flowered naturally as field grown plants from plantings made in mid-June and given a single pinch.
(5) Averages three more breaks per plant when flowered naturally as field grown plants from plantings made in mid-June and given a single pinch.

(6) A lighter foilage color.
(7) A more coarsely indented and serrated foilage.

The new cultivar was selected from the progeny of the designated cross and when asexually preproduced by cuttings at Barberton, Ohio, has been found to retain its distinctive characteristics through successive propagations.

The new cultivar when grown in the vicinity of Barberton, Ohio, has a response period of approximately 7 weeks, and the following detailed description is based on observations made of the new cultivar at and in a greenhouse in Barberton, Ohio. The response time, blooming period, color, and total vigor may vary significantly with varying environmental conditions such as temperature, day length, and light intensity. Suggested flowering in the northern and western United States is from April through May and September through October; Florida, January through February.

The accompanying color photographic drawings show the unique characteristics of the new cultivar, with the color being as nearly true as possible with color illustrations of this type. Sheet 1 comprises an illustration of the new cultivar by itself, and Sheet 2 comprises a comparison photograph, with the new cultivar appearing on the left and the cultivar White Grandchild on the right. It should be noted that in the specimen photograph (Sheet 1), the tips of certain of the petals appear to be slightly blue or gray, perhaps because of the background of the photograph. The true color of the flower petals is best shown in the comparison photograph.

In the following description, color references are made to the Munsell Color Book, 1963 edition, and comparisons are made with the cultivar White Grandchild. Where only a single value or description appears for the new cultivar, the same value or description applies as well to the comparison cultivar.

Botanical classification: *Chrysanthemum morifolium*

| | Cloud-9 | White Grandchild |
|---|---|---|
| Bloom: | | |
| Size | Approximately 4½″ non- disbudded<br>Approximately 5″ disbudded | Approximately 1½″ non-disbudded. |
| Fully expanded | Approximately 5″ non-disbudded<br>Approximately 5½″ disbudded. | Approximately 2″ non-disbudded. |
| Borne | Clusters on elongated pedicels | |
| Stems | Strong | |
| Form | Semi-incurve | Decorative. |
| Permanence | 10 days | |
| Color: | | |
| Center of flower | Light yellow, 7.5Y8.5/10 | White, N9.5/. |
| Base of petals | Green, 2.5GY8/10 | Do. |
| Inside of petals | Light yellow, 7.5Y9/6 to ivory, 10Y9/1 | White, N9.5/. |
| Reverse of petals | White, N9.5/ | |
| Tonality from a distance | Ivory white | White. |
| Discoloration | White, N9/ | Light lavender pink, 7.5RP9/2 over white, N9.5/ with lavender tones increasing with age. |
| Petals: | | |
| Texture | Smooth | |
| Appearance and form | Closed at base, broadening to a deeply ridged keel, tapering to a blunt notched point. | Open at base, broad shallow keel; tapering to a blunt point. |
| Arrangement | Composite, whorled on a single receptacle | |
| Persistence | Resist shatter | |
| Fragrance | Typical chrysanthemum | |
| Reproductive organs: | | |
| Stamen, anthers | 0–20 | |
| Pollen | None to scant | |
| Arrangements | Clustered in center of flower, if present | |
| Styles | Present both ray and disc florets | |
| Length | Short | |
| Ovaries | At the base of petal attached to receptacle | |
| Plant: | | |
| Form | Herbaceous | |
| Growth | Compact-spreading | |
| Height | Approximately 12″ when flowered naturally as field grown plants from plantings made in mid-June and given a single pinch. | Approximately 14″ when flowered naturally as field grown plants from plantings made in mid-June and given a single pinch. |
| Spread | Approximately 20″ when flowered naturally as field grown plants from plantings made in mid-June and given a single pinch. | |
| Foliage: | | |
| Top side | Dark green, 7.5GY3/4 | Dark green, 10GY2/4. |
| Size | 4¼″ long, 3¼″ wide | 3″ long, 2″ wide. |
| Quantity | Numerous | |
| Shape | Spatulate lobed | |
| Texture | Coarse | Smooth. |
| Ribs and veins | Moderately prominent | Prominent. |
| Edge | Deeply indented | Moderately indented. |
| Serration | Moderate | Very slight. |
| Under side | Light green, 7.5GY5/4 | |
| Stipules | Rudimentary | |

We claim:

1. A new and distinct cultivar of chrysanthemum characterized particularly as to its uniqueness when compared to the cultivar White Grandchild by its flowers which are approximately 2½ inches to 3 inches larger in diameter, and which are more ivory white in color, and do not pink with age; by its growth habit which produces flowerng plants which are approximately three inches shorter in height and which average three more breaks per plant when flowered naturally as field grown plants from plantings made in mid-June and given a single pinch; and by its foilage, which is lighter green in color and which is more coarsely indented and more moderately serrated.

No references cited.

ROBERT E. BAGWILL, Primarv Examiner